(12) United States Patent
Raulerson et al.

(10) Patent No.: US 7,368,907 B2
(45) Date of Patent: May 6, 2008

(54) OMNI-DIRECTIONAL ELECTRIC CURRENT PERTURBATION PROBE

(75) Inventors: David A. Raulerson, Palm Beach Garden, FL (US); Kevin D. Smith, Glastonbury, CT (US)

(73) Assignee: United Technologies Corporation, Hartford, CT (US)

( * ) Notice: Subject to any disclaimer, the term of this patent is extended or adjusted under 35 U.S.C. 154(b) by 0 days.

(21) Appl. No.: 11/488,295

(22) Filed: Jul. 18, 2006

(65) Prior Publication Data

US 2008/0018331 A1    Jan. 24, 2008

(51) Int. Cl.
*G01N 27/72* (2006.01)
*G01N 27/82* (2006.01)

(52) U.S. Cl. ............ 324/238; 324/228; 324/234; 324/239; 324/240

(58) Field of Classification Search ........ 324/228, 324/240, 230, 232, 233, 234, 236, 237, 238, 324/239
See application file for complete search history.

(56) References Cited

U.S. PATENT DOCUMENTS

| | | | |
|---|---|---|---|
| 4,430,615 A * | 2/1984 | Calvert | 324/239 |
| 5,754,043 A * | 5/1998 | Logue | 324/207.26 |
| 6,040,695 A | 3/2000 | Raulerson et al. | |
| 6,888,347 B2 * | 5/2005 | Batzinger et al. | 324/242 |

FOREIGN PATENT DOCUMENTS

| | | |
|---|---|---|
| FR | 2780510 A1 * | 12/1999 |
| JP | 2002131285 A * | 5/2002 |

* cited by examiner

*Primary Examiner*—Patrick Assouad
*Assistant Examiner*—David M. Schindler
(74) *Attorney, Agent, or Firm*—Carlson, Gaskey & Olds

(57) ABSTRACT

An electric current perturbation probe includes at least one driver coil and at least one receiver. The at least one driver coil produces an omni-directional magnetic field. The at least one receiver is decoupled from the omni-directional magnetic field. In one example, the at least one driver coil includes a first driver coil that defines a first effective coil axis which is positioned orthogonally to a second effective coil axis of a second driver coil. The first driver coil is provided with a first electrical excitation signal which is phase shifted by 90 degrees from a second electrical excitation signal used to drive the second driver coil.

12 Claims, 5 Drawing Sheets

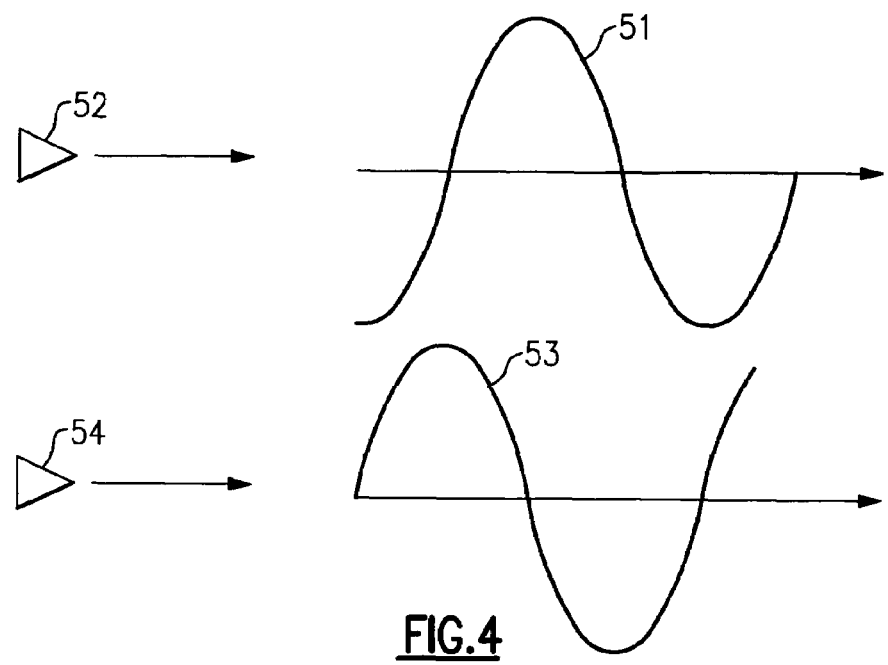
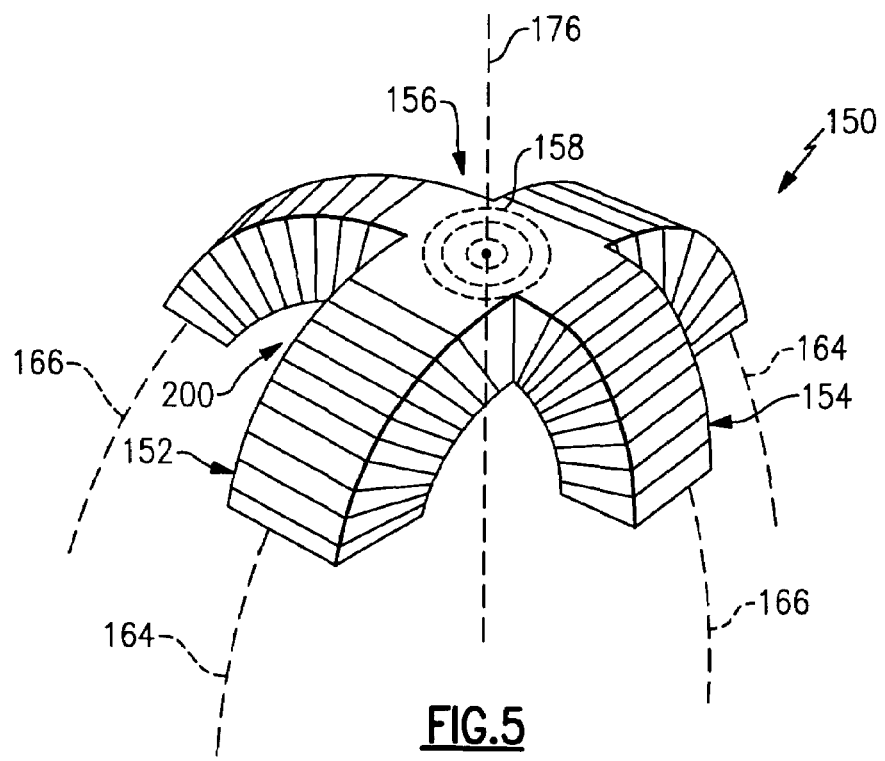

OMNI-DIRECTIONAL ELECTRIC CURRENT PERTURBATION PROBE

BACKGROUND OF THE INVENTION

The present invention generally relates to inspection systems, and more particularly to an electric current perturbation probe having omni-directional sensitivity capabilities.

Inspection systems having eddy current probes are often used for non-destructive evaluation (NDE) of critical components in the aerospace and power generation industries. Many components in these industries must endure extremely high stresses in the course of operation. It is necessary to detect even minute flaws in order to ensure the durability of these components. For example, a rotor disk for a gas turbine engine must have its entire surface inspected in order to detect the presence of defects. An inability to detect defects of a certain size or orientation can prevent the production of higher performance and more competitive products, and may lead to safety concerns regarding the product.

Known eddy current probes typically include a driver coil and at least one receiver coil. The driver coil is provided with an electrical excitation signal (i.e. an electrical current) and generates an alternating electromagnetic field that results in a magnetic field in a component under inspection as the probe is moved along a path above the component's surface. The magnetic field creates an eddy current in and near the surface of a component fabricated from a conductive material. The eddy currents in the component under inspection result in an electromagnetic signal or response, which is received within the receiver coil and detected by commercial instrumentation. As the eddy current probe passes over an anomaly, e.g., a flaw or a different morphology in the component, the anomaly disrupts the eddy currents and results in a different signal received by the receiver coil. The change between the signal received by the receiver coil and the signal generated within the driver coil is detected by the commercial instrumentation.

One type of eddy current probe is referred to as an electric current perturbation (ECP) probe. An ECP probe defines a driver core axis which is perpendicular to a receiver core axis. This feature decouples the driver magnetic field from a receiver, thereby reducing the sensitivity of the receiver to surface noise that does not represent a defect.

Although ECP probes typically provide high sensitivity, these probes are directionally sensitive in a single direction. That is, known ECP probes have a unidirectional sensitivity characteristic. Therefore, the ECP probes may only detect a flaw in the component where the orientation of the flaw is aligned directly with the directional sensitivity of the probe. Many components include complex surfaces that define complicated part stresses which may include flaws having an arbitrary orientation which is not aligned with the directional sensitivity of the electric current perturbation probe. Disadvantageously, the arbitrary orientation of the flaw may result in the flaw being unidentified by the electric current perturbation probe. The inability to detect flaws of a certain orientation can prevent production of higher performance and more competitive products, and may lead to safety concerns.

Accordingly, it is desirable to provide an omni-directional electric current perturbation probe that achieves increased sensitivity and that is disruptible in multiple directions.

SUMMARY OF THE INVENTION

An example electric current perturbation probe includes at least one driver coil and at least one receiver. The at least one driver coil produces an omni-directional magnetic field. The at least one receiver is decoupled from the omni-directional magnetic field. In one example, the at least one driver coil includes a first driver coil that defines a first effective coil axis which is positioned orthogonally to a second effective coil axis of a second driver coil. The first driver coil is provided with a first electrical excitation signal which is phase shifted by 90 degrees from a second electrical excitation signal used to drive the second driver coil.

A second example electric current perturbation probe includes at least one driver coil that produces an omni-directional magnetic field, a solenoidal driver core that at least partially surrounds the at least one driver coil, and a plurality of receivers positioned near an end of the solenoidal driver core. The plurality of receivers are decoupled from the omni-directional magnetic field.

An example inspection system includes an interface instrument, a processor and an eddy current probe which houses an electric current perturbation probe element. The electric current perturbation probe element includes a driver core, a first driver coil, a second driver coil and at least one receiver. The first driver coil defines a first effective coil axis which is orthogonal to a second effective coil axis defined by the second driver coil. In one example, the driver core comprises a rectangular shape. In another example, the driver core comprises a semi-toroidal shape.

The various features and advantages of this invention will become apparent to those skilled in the art from the following detailed description. The drawings that accompany the detailed description can be briefly described as follows.

BRIEF DESCRIPTION OF THE DRAWINGS

FIG. 4 illustrates a graphical view of example electrical excitation signals for rotating the magnetic fields of the electric current perturbation probe according to the present invention;

FIG. 5 is a second example electric current perturbation probe according to the present invention;

DETAILED DESCRIPTION OF THE PREFERRED EMBODIMENT

Figure 1:
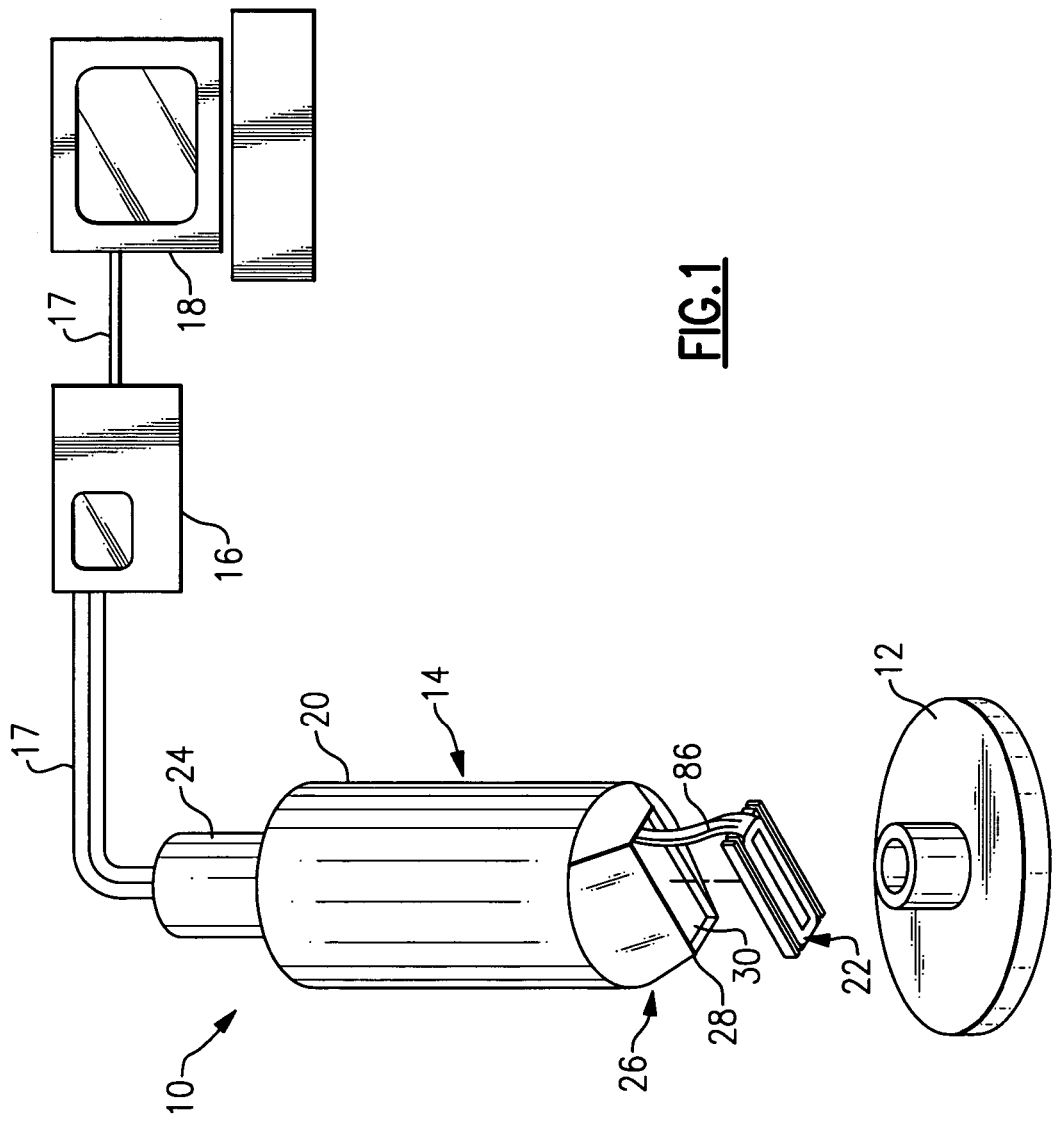
FIG. 1 illustrates an automated inspection system according to the present invention.

Referring to FIG. 1, an automated inspection system 10 for inspecting an object 12 for surface defects, such as a rotor disk for a gas turbine engine, is illustrated. The automated inspection system 10 includes an eddy current probe 14, an interface instrument 16 and a processor 18. In one example, the eddy current probe 14 is an electric current perturbation (ECP) probe. The eddy current probe 14 comprises a housing 20, a probe element 22 and an electrical connector 24. The eddy current probe 14, the interface instrument 16 and the processor 18 are electrically connected via a plurality of electrical conductors 17. The housing 20 has an end 26 with an outer surface 28 and a cavity 30. The probe element 22 is positioned within the cavity 30.

Figure 2:
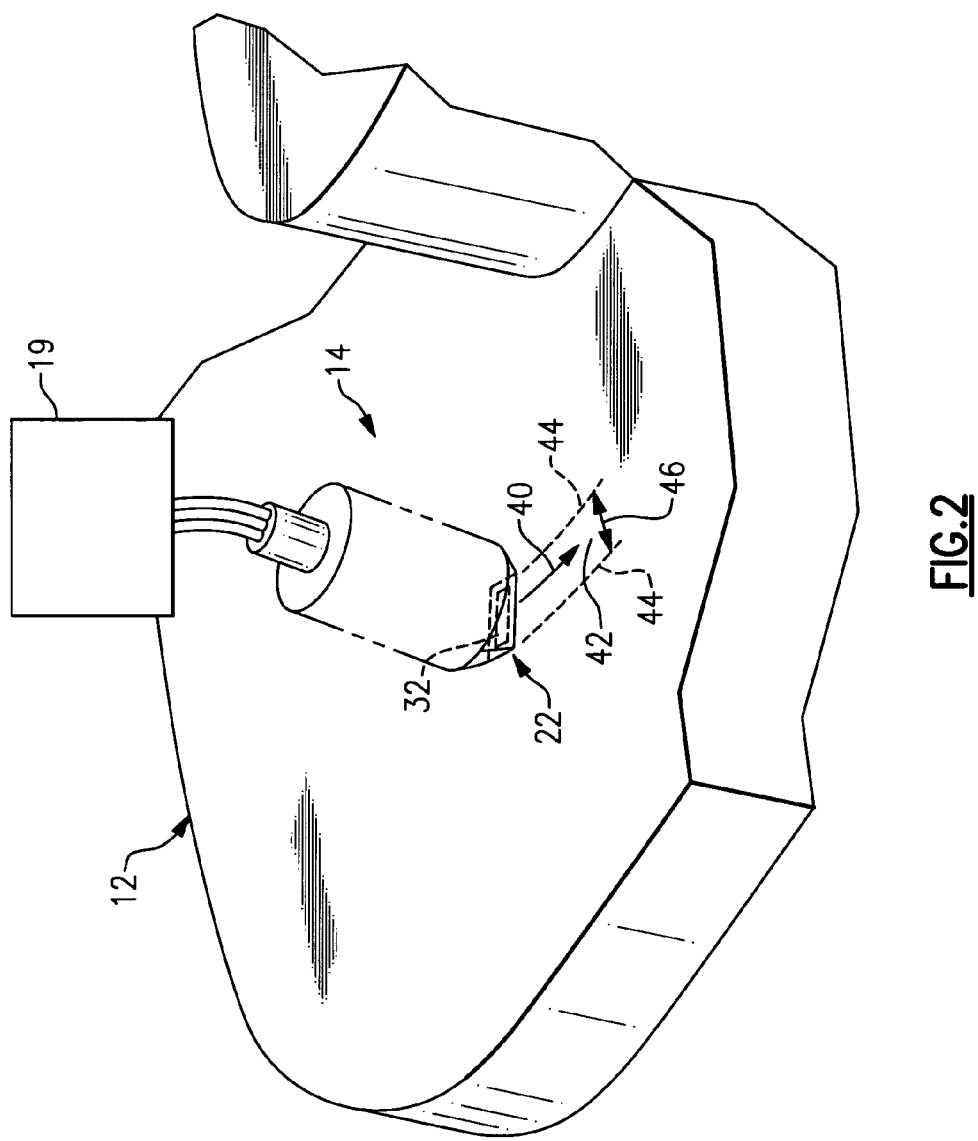
FIG. 2 illustrates a use of the automated inspection system for detecting a defect in an object.

Referring to FIG. 2, an automated manipulator (i.e., a robot) shown schematically at 19, positions the eddy current probe 14 adjacent to a surface of the object 12 under examination to facilitate inspection of the surface. The manipulator orients the eddy current probe 14 towards the object 12 under inspection. This orientation facilitates inspection of a scan surface 32 of the object 12 under examination, which is that surface directly underneath the probe element 22. The interface instrument 16 provides an electrical excitation signal to the eddy current probe 14 that results in the generation of a magnetic field from the eddy current probe 14. In one example, the electrical excitation signal comprises a time varying signal, such as a sine wave. The magnetic field generated by the eddy current probe 14 creates an eddy current in the scan surface 32 of the object 12. The characteristics of the eddy current created in the object 12 depend upon the characteristics of the scan surface 32 of the object. That is, the characteristics of the eddy currents created in the object 12 will depend on whether the scan surface 32 of the object 12 has any defects. The eddy current created in the scan surface 32 of the object 12 results in an electrical signal received by the eddy current probe 14. The electrical signal has characteristics commensurate with those of the eddy current in the object 12.

The manipulator 19 moves the eddy current probe 14 in a scanning path 40 which is generally parallel to the outer surface of the object 12 being scanned. As the eddy current probe 14 moves along the scanning path 40, it scans the object 12 which is directly underneath the probe element 22 resulting in a cumulative scanned surface 42 outlined by a pair of dotted lines 44. The cumulative scan surface has a width 46.

The interface instrument 16 monitors the eddy current signal returned from the object 12 to determine whether a defect or flaw exists therein. The current signal received from the object 12 is provided to the processor 18 to determine whether a true defect exists in the scan surface 32 of the object 12. In one example, the processor 18 is a personal computer. The processor 18 examines the eddy current signal returned from the object 12 for disruptions in the signal relative to the electrical excitation signal originally provided to the eddy current probe 14.

Figure 3:
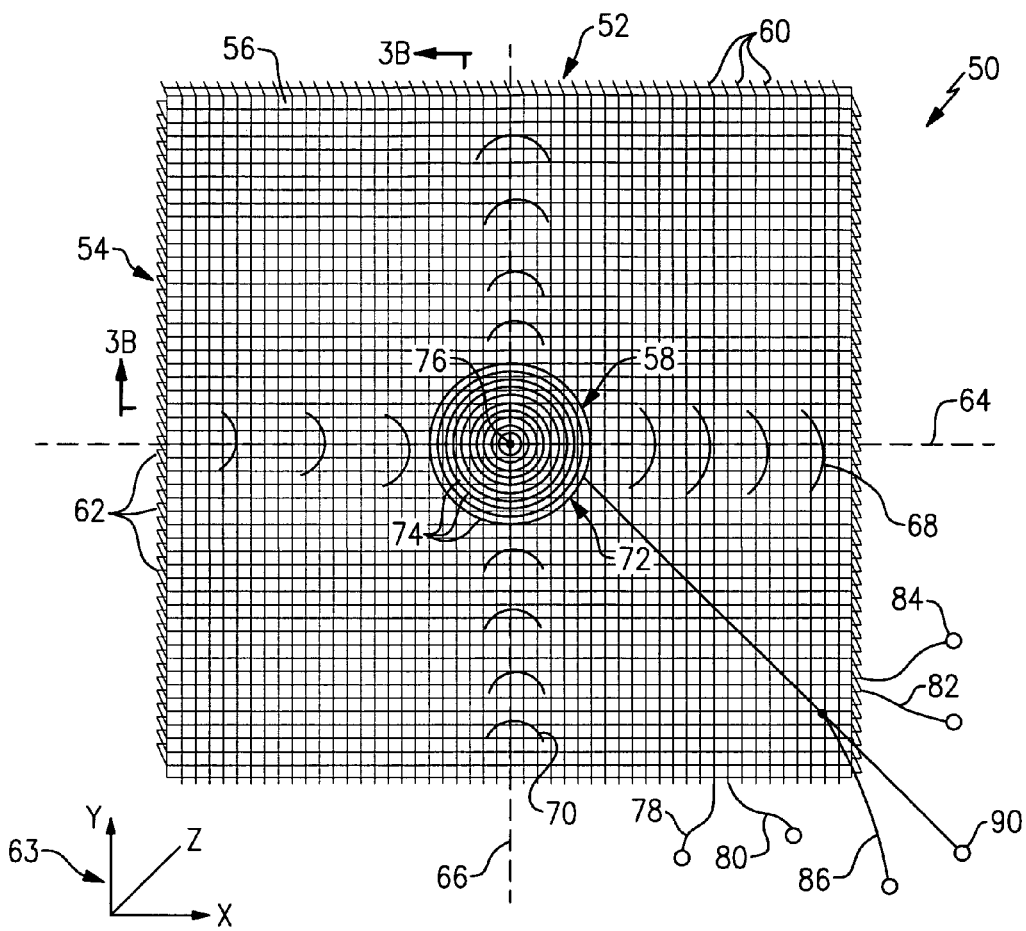
FIG. 3 illustrates a first example electric current perturbation probe according to the present invention.
Figure 3A:
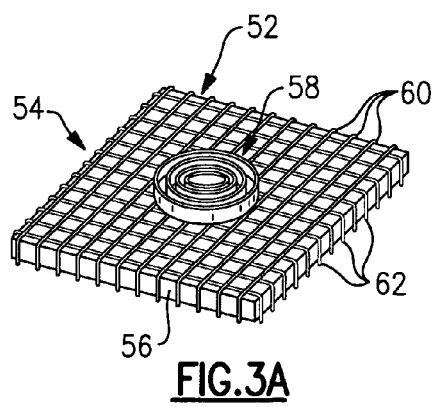
FIG. 3A illustrates a perspective view of the electric current perturbation probe shown in FIG. 3.
Figure 3B:
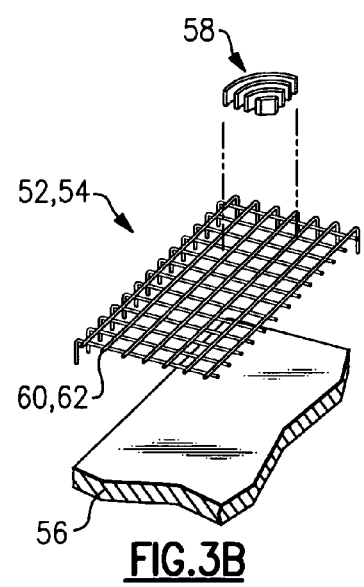
FIG. 3B illustrates an exploded sectional view of section 3B-3B of FIG. 3.

Referring to FIGS. 3, 3A and 3B, an electric current perturbation (ECP) probe 50 for use as the probe element in the automated inspection system 10 shown in FIGS. 1 and 2 is illustrated. The ECP probe 50 includes a first driver coil 52, a second drive coil 54, a driver core 56, and at least one receiver 58. The first driver coil 52 and the second driver coil 54 each include a plurality of windings 60, 62 disposed around the driver core 56 (See FIG. 3B). In this example, the driver core 56 has the shape of a rectangular block. A person of ordinary skill in the art would understand that the driver core 56 may include any known shape to provide an omni-directional ECP probe according to the present invention.

The driver core 56 comprises a permeable material. In one example, the driver core 56 is a plastic core. In another example, the driver core 56 comprises a ferrite core material. The windings 60 of the first driver coil 52 are disposed around the driver core 56 to define a first effective coil axis 64, which is positioned on an x-axis of a coordinate system 63. The windings 62 of the second driver coil 54 are wound around the driver core 56 to define a second effective coil axis 66, which is positioned on a y-axis of the coordinate system 63, that is transverse to the first effective coil axis 64. In one example, the windings 60, 62 of the first driver coil 52 and the second driver coil 54 are comprised of copper wire having an enamel insulation, although any suitable electrical conductor may be used.

The first effective coil axis 64 and the second effective coil axis 66 define a primary apparent axis of the first driver coil 52 and the second driver coil 54, respectively. That is, the first effective coil axis 64 is substantially parallel to the primary direction of a first magnetic field 68 produced by the first driver coil 52, and the second effective coil axis 66 is substantially parallel to the primary direction of a second magnetic field 70 which is produced by the second driver coil 54. In one example, the first effective coil axis 64 is orthogonal to the second effective coil axis 66 to provide omni-directional field sensitivity, as is further discussed below. Although an orthogonal driver configuration is shown and described herein, it should be understood that other configurations are contemplated by the present invention.

The receiver 58 includes a coil 72 having a plurality of windings 74. In one example, the coil 72 of the receiver 58 is a flat coil having a pancake like shape and includes a single layer of windings 74. However, the ECP probe 50 may include any number of receivers. For example, the ECP probe 50 may include an array of receiving elements that provide spatial information to the interface instrument 16. In another example, the receiver 58 is comprised of 50 gauge copper wire with an enamel insulation. It should be understood that any known receiver type or material, including but not limited to wire wound, printed circuit, photo-lithographic and vapor deposition elements, may be utilized as the receiver for the electric current perturbation probe of the present invention.

The receiver 58 is affixed to the driver core 56 in a known manner. In one example, the receiver 58 is affixed to the driver core 56 with a small amount of adhesive placed between the driver core 56 and the receiver 58.

The coil 72 of the receiver 58 defines a receiver effective axis 76 (positioned on a z-axis, i.e. into the page, of the coordinate system 63) which is oriented transverse to each of the first effective coil axis 64 and the second effective coil axis 66. In one example, the receiver effective axis 76 is substantially perpendicular to the first effective coil axis 64 and the second effective coil axis 66. The perpendicular orientation of the receiver effective axis 76 with respect to the driver effective coil axes 64 and 66 decouples the receiver 58 from the magnetic fields 68, 70 of the first driver coil 52 and the second driver coil 54, respectively. Therefore, the ECP probe 50 is less sensitive to the surface morphology of an object 12 during inspection. That is, the ECP probe 50 is less sensitive to surface noise that does not represent a defect.

The first driver coil 52 includes two end terminals 78, 80 and the second driver coil 54 includes two end terminals 82, 84. In one example, the receiver 58 also includes two end terminals 86 and 90. A person of ordinary skill in the art would understand that the number of end terminals utilized in the ECP probe 50 depends upon application specific parameters. One end terminal of each of the first driver coil 52, the second driver coil 54 and the receiver 58 is connected to ground. The other end terminal of each of the first driver coil 52, the second driver coil 54 and the receiver 58 is electrically connected to the interface instrument 18 in a known manner. The interface instrument 18 provides a first electrical excitation signal to the first driver coil 52 and a second electrical excitation signal to the second driver coil 54. The first electric excitation signal and the second electrical excitation signal result in a first current that flows through the first driver coil 52 and a second current which flows through the second driver coil 54.

Referring to FIG. 4, the first and second electrical excitation signals are comprised of a time varying signal to electrically rotate the magnetic fields 68, 70 of the first driver coil 52 and the second driver coil 54, respectively. For example, the first driver coil 52 is driven by a cosine wave 51 frequency and the second driver coil 54 is driven by a sine wave 53 frequency. That is, the first electrical excitation signal and the second electrical excitation signal are phase shifted by 90 degrees. Providing the first driver coil 52 and the second drive coil 54 with phase shifted electrical excitation signals results in the continuous rotation of the first magnetic field 68 and the second magnetic filed 70. Because of the orthogonal positioning of the first driver coil 52 with respect to the second driver coil 54, and because the magnetic fields 68, 70 created by the first driver coil 52 and the second driver coil 54 are continuously rotated by supplying phase shifted electrical excitation signals, the ECP probe 50 of the present invention is provided with omni-directional sensitivity capabilities which allow the probe 50 to detect flaws which may be arbitrarily oriented on the surface of an object 12 under inspection.

In another example, magnetic fields 68, 70 of the first driver coil 52 and the second driver coil 54 are electrically rotated by modulating the amplitude of the first electrical excitation signal with respect to the second electrical excitation signal. The first driver coil 52 and the second driver coil 54 are therefore provided with electrical excitation signals that include equal frequencies and phases. In this way, the rotation of the magnetic fields 68, 70 is controlled independently from the frequency provided to drive the driver coils 52, 54, respectively.

Referring to FIG. 5, a second example ECP probe 150 is illustrated. The ECP probe 150 includes a driver core 156 having a semi-toroidal shape. A semi-toroid has a circular volume with a rectangular cross section. The ECP probe 150 includes a first driver coil 152, a second driver coil 154, and a receiver 158. The first driver coil 152 and the second driver coil 154 are disposed around the driver core 156, with the first driver coil 152 being positioned transversely to the second driver coil 154. In one example, the first driver coil 152 is positioned orthogonally to the second driver coil 154 such that effective axes 164, 166 of the first driver coil 152 and the second driver coil 154 are orthogonal to one another.

The receiver 158 is affixed to the driver core 156 on a bottom side 200 of the driver core 156. In another example, the receiver 158 is received within a plane defined by the semi-toroidal shape of the driver core 156. Although one flat, single layer coil type receiver is depicted, it should be understood that any receiver type and amount may be utilized with the ECP probe 150 according to the present invention. The receiver 158 also defines a receiver effective axis 176 which is oriented substantially perpendicular to the effective axes 164, 166 of the first driver coil 152 and the second driver coil 154. Therefore, the receiver 158 is decoupled from the first driver coil 152 and the second driver coil 154 thereby making the probe 150 less sensitive to the surface morphology of the object under inspection. The first driver coil 152, the second driver coil 154 and the receiver 158 are connected together and to the interface instrument 18 in an identical manner as that shown in FIG. 3 with respect to the ECP probe 50 (i.e. via the end terminals and common terminals 78-90).

Omni-directional signal sensitivity is created with the electric current perturbation probe 150 in a similar manner as that utilized to create the Omni-directional signal sensitivity of the electric current perturbation probe 50 shown in FIGS. 1-4. That is, the magnetic fields created by each of the first driver coil 152 and the second driver coil 154 are continuously rotated by supplying a time varying signal which is phase shifted by 90° to create the desired omni-directional field sensitivity. In other words, the example ECP probe 150 is identical to the ECP probe 50 except that the ECP probe 150 includes a driver core 156 which is semi-toroidal rather than rectangular.

Figure 6:
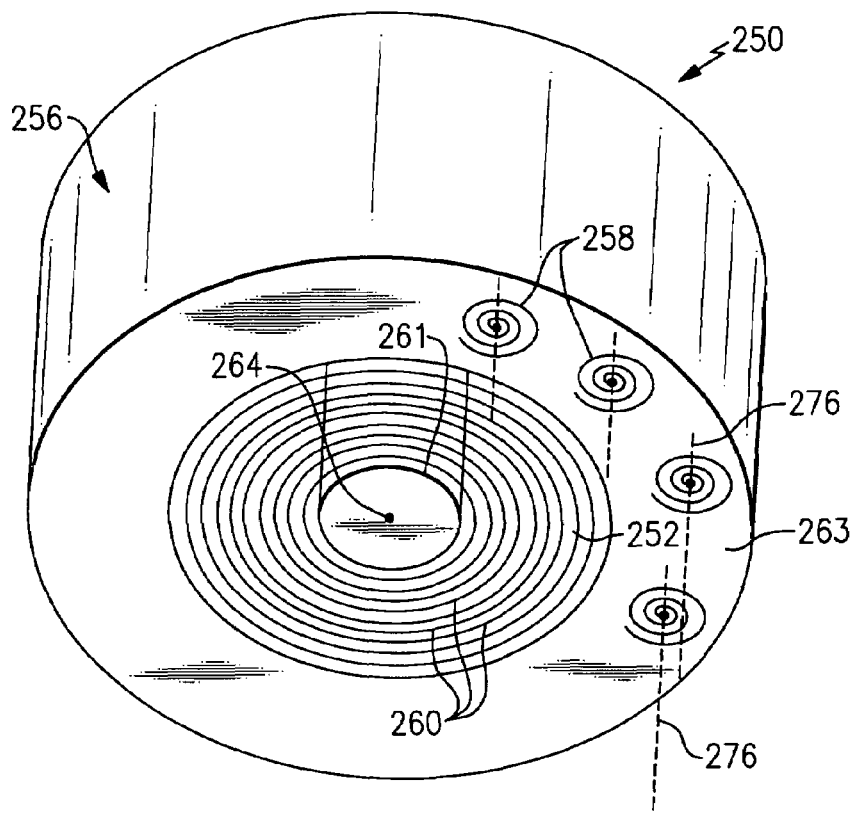
FIG. 6 illustrates yet another example electric current perturbation probe according to the present invention.

Referring to FIG. 6, another example ECP probe 250 is illustrated. In this example, the ECP probe's geometry generates the desired omni-directional signal sensitivity. The ECP probe 250 includes a driver coil 252, a solenoidal driver core 256 and a plurality of receivers 258. The driver coil 252 includes a plurality of windings 260 coiled within a cup core 261 of the solenoidal driver core 256. In one example the driver coil 252 includes windings 260 having twenty layers with ten turns per layer.

In one example, the ECP probe 250 includes four receivers 258. The four receivers 258 may be flat, single layer coils. However, any known receiver type may be utilized by the ECP probe 250. A person of ordinary skill in the art would understand that the actual number of receivers utilized will depend upon application specific parameters such as physical limitations inherent in the shape of the receiver core, the availability of multi-channel interface instruments, and the desired size of the receivers.

The receivers 258 are disposed radially on an exterior flange 263 of a cup core 261 of the solenoidal driver core 256 over a range of about 90°. Each receiver 258 therefore receives an electrical signal from the object 12 under examination according to the position of that receiver 258 relative to the object 12 such that the interface instrument 16 may analyze the signal no matter how the ECP probe 250 is oriented. The effective axes 276 defined by each of the receivers 258 are transverse to a center 264 of the driver coil 252. In one example, the effective axes 276 are parallel to the center 264 of the driver coil 252. Therefore, the receivers 258 are decoupled from the magnetic field generated by the driver coil 252 to provide the sensitivity characteristics of an ECP probe.

An electrical excitation signal, such as an electrical current, is provided to the driver coil 252 to generate a magnetic filed (not shown) below the driver coil 252. The magnetic field created by the electric current perturbation probe 250 is rotational and therefore supports omni-directional requirements based solely upon the geometry of the driver core 256.

Figure 7:
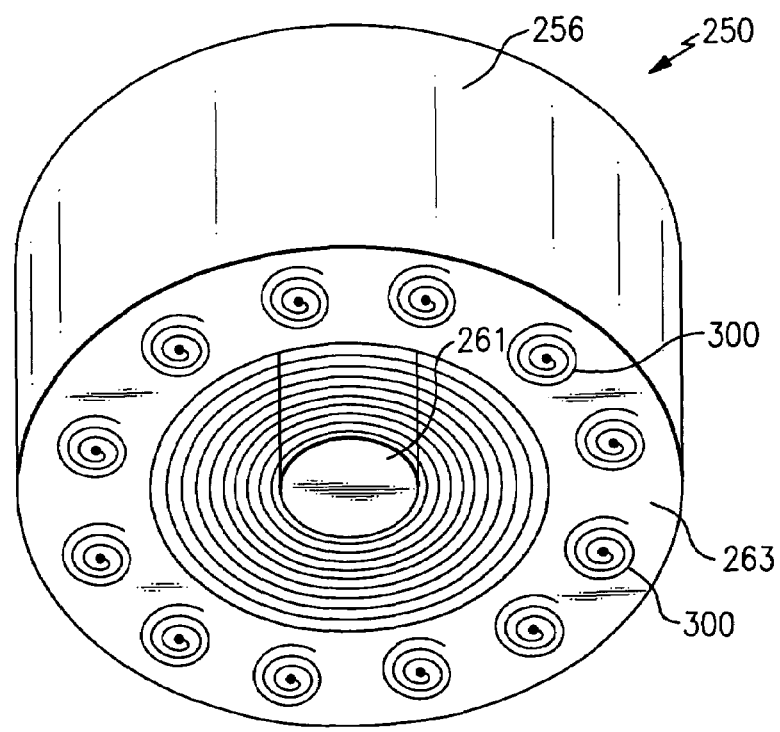
FIG. 7 illustrates an example receiver configuration for the electric current perturbation probe as illustrated in FIG. 6.

In another example, additional receivers are utilized to improve the sensitivity of the ECP probe 250. For example, as shown in FIG. 7, twelve receivers 300 are positioned radially about the exterior flange 263 of the cup core 261 of the solenoidal driver core 256. In this example, the twelve receivers 300 are flat, single layer coils, although any known receiver may be utilized. Each receiver 300 is uniformly spaced about the exterior flange 263 of the cup core 261 over 360°.

The foregoing description shall be interpreted as illustrative and not in any limiting sense. A worker of ordinary skill in the art would recognize that certain modifications will come within the scope of this invention. For that reason, the following claims should be studied to determine the true scope and content of this invention.

What is claimed is:

1. An electric current perturbation probe, comprising:
   a driver core having a semi-toroidal shape;
   at least two driver coils disposed about said driver core and producing an omni-directional magnetic field; and
   at least one receiver decoupled from said omni-directional magnetic field.

2. The electric current perturbation probe as recited in claim 1, wherein said at least one receiver is affixed to said driver core on a bottom side of said driver core.

3. The electric current perturbation probe as recited in claim 1, wherein said at least one receiver is received within a plane defined by said semi-toroidal shape of said driver core.

4. The probe as recited in claim 1, wherein said at least two driver coils comprises a first driver coil that defines a first effective coil axis and a second driver coil that defines a second effective coil axis, wherein said first effective coil axis is different from said second effective coil axis.

5. The probe as recited in claim 4, wherein said first driver coil and said second driver coil are disposed around said driver core.

6. The probe as recited in claim 4, further comprising an interface instrument operable to provide a first electrical excitation signal to said first driver coil to rotate a first magnetic field and a second electrical excitation signal to said second driver coil to rotate a second magnetic field.

7. The probe as recited in claim 6, wherein the rotation of said first magnetic field and said second magnetic field creates said omni-directional magnetic field, wherein said first electrical excitation signal is phase shifted 90 degrees from said second electrical excitation signal.

8. The probe as recited in claim 6, wherein said at least one receiver communicates with said interface instrument to receive current signals.

9. The probe as recited in claim 4, wherein said first effective coil axis is orthogonal to said second effective coil axis.

10. The probe as recited in claim 4, wherein a receiver effective axis defined by said at least one receiver is transverse to said first effective coil axis and said second effective coil axis.

11. The probe as recited in claim 4, wherein said first driver coil is transverse to said second driver coil.

12. The probe as reicted in claim 11, wherein said first driver coil is orthogonal to said second driver coil.

* * * * *